United States Patent
Dayton

(10) Patent No.: US 9,657,319 B2
(45) Date of Patent: May 23, 2017

(54) PROCESS FOR PRODUCTION OF LOW SATURATE OILS

(71) Applicant: Christopher L. G. Dayton, White Plains, NY (US)

(72) Inventor: Christopher L. G. Dayton, White Plains, NY (US)

(73) Assignee: BUNGE GLOBAL INNOVATION LLC, White Plains, NJ (US)

( * ) Notice: Subject to any disclaimer, the term of this patent is extended or adjusted under 35 U.S.C. 154(b) by 322 days.

(21) Appl. No.: 13/917,488

(22) Filed: Jun. 13, 2013

(65) Prior Publication Data

US 2013/0337515 A1  Dec. 19, 2013

Related U.S. Application Data

(60) Provisional application No. 61/659,867, filed on Jun. 14, 2012.

(51) Int. Cl.

| | | |
|---|---|---|
| *C12P 7/64* | (2006.01) | |
| *G11B 3/00* | (2006.01) | |
| *C11C 1/04* | (2006.01) | |
| *C11B 1/02* | (2006.01) | |
| *C11B 3/00* | (2006.01) | |

(52) U.S. Cl.
CPC .......... *C12P 7/6418* (2013.01); *C11B 1/025* (2013.01); *C11B 3/003* (2013.01); *C11C 1/045* (2013.01)

(58) Field of Classification Search
CPC ......... C11B 1/025; C11B 3/003; C11C 1/045; C12P 7/6418
See application file for complete search history.

(56) References Cited

U.S. PATENT DOCUMENTS

| | | | |
|---|---|---|---|
| 4,049,686 A | | 9/1977 | Ringers et al. |
| 4,671,902 A | * | 6/1987 | Brister .................. 554/179 |
| 4,698,185 A | | 10/1987 | Dijkstra et al. |
| 5,006,281 A | * | 4/1991 | Rubin et al. .................. 554/3 |
| 5,239,096 A | | 8/1993 | Borodi et al. |
| 5,264,367 A | | 11/1993 | Aalrust et al. |
| 5,286,886 A | | 2/1994 | Van de Sande et al. |
| 5,532,163 A | | 7/1996 | Yagi et al. |
| 6,001,640 A | | 12/1999 | Loeffler et al. |
| 6,103,505 A | | 8/2000 | Clausen et al. |
| 6,127,137 A | | 10/2000 | Hasida et al. |
| 6,143,545 A | | 11/2000 | Clausen et al. |
| 6,172,248 B1 | | 1/2001 | Copeland et al. |
| 6,248,911 B1 | * | 6/2001 | Canessa et al. ............. 554/191 |
| 6,548,633 B1 | | 4/2003 | Edwards et al. |
| 7,226,771 B2 | | 6/2007 | Gramatikova et al. |
| 7,312,062 B2 | | 12/2007 | Bojsen et al. |
| 7,494,676 B2 | | 2/2009 | Chakrabarti et al. |
| 7,713,727 B2 | | 5/2010 | Dayton et al. |
| 8,153,391 B2 | | 4/2012 | Dayton et al. |
| 8,192,782 B2 | | 6/2012 | Soe et al. |
| 8,357,503 B2 | | 1/2013 | Dayton et al. |
| 2008/0182322 A1 | | 7/2008 | Dayton et al. |
| 2009/0069587 A1 | | 3/2009 | Dayton et al. |
| 2010/0129882 A1 | | 5/2010 | Dayton et al. |
| 2010/0224563 A1 | * | 9/2010 | Singh et al. ................. 210/651 |
| 2011/0136187 A1 | | 6/2011 | Soe et al. |

FOREIGN PATENT DOCUMENTS

| | | |
|---|---|---|
| CN | 1293706 A | 5/2001 |
| CN | 1931983 A | 3/2007 |
| CN | 102325891 A | 1/2012 |
| WO | 99/53001 A1 | 10/1999 |
| WO | 2010/024924 A2 | 3/2010 |

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Bergers et al., "Enzymatic Distinction Between Two Subgroups of Autosomal Recessive Lamellar Ichthyosis," The journal of investigative dermatology, 94(4):407-412 (1990).
Tandy et al., "Physical Refining of Edible Oil," JAOCS, 61(7):1253-1258 (1984).
Bailey, A. E. (1950). Melting and Solidification of Fats, Interscience Publishers, Inc., New York. Chapter 1, pp. 22-24 section 7, Polymorphism. Chapter 3, pp. 165-168, section (c) Mixed Unsaturated Triglycerides.
Soleimanian et al., "Influence of processing parameters on physicochemical properties of fractionated fish oil at low temperature crystallization," Nutrition & Food Science 45(1):2-19 (2015).

\* cited by examiner

*Primary Examiner* — Delia Ramirez
(74) *Attorney, Agent, or Firm* — Jones Day

(57) ABSTRACT

Provided here is an enzymatic process for production of low saturate oil, in one embodiment, low palmitic oils from triacylglycerol sources. The enzymes used in the processes herein are saturase enzymes, including palmitase enzymes. The oils produced by the processes herein are used in food products.

9 Claims, 1 Drawing Sheet

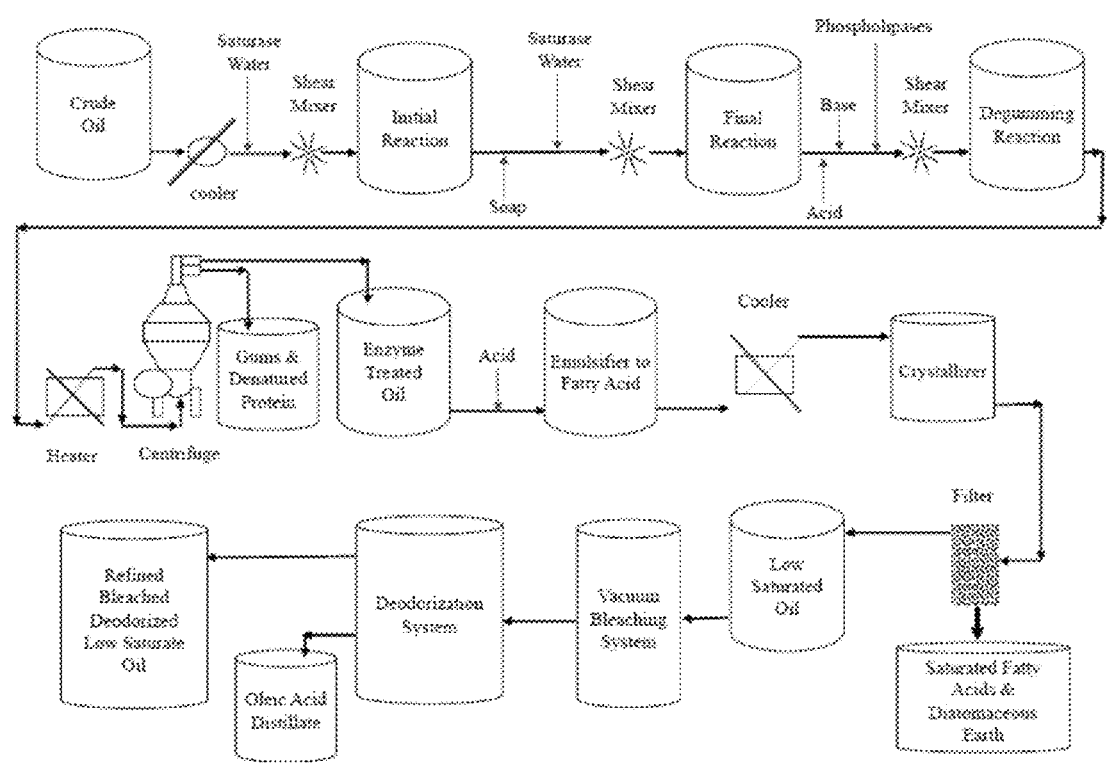

PROCESS FOR PRODUCTION OF LOW SATURATE OILS

CROSS REFERENCE TO RELATED APPLICATIONS

This application claims the benefit of the priority of U.S. Provisional Application No. 61/659,867, filed Jun. 14, 2012, the disclosure of which is incorporated herein by reference in its entirety.

SEQUENCE LISTING

The present application is being filed with a Sequence Listing submitted as filename 011631-079-999 _SeqListing.txt, of size 6,167 bytes, which was created on Jun. 10, 2013. The Sequence Listing is incorporated herein by reference in its entirety.

FIELD

Provided herein is an enzymatic process for production of low saturate oils from triacylglycerol sources. The enzymes used in the processes herein are saturase enzymes. The oils produced by the processes herein may be used in food products.

BACKGROUND

Diets with high levels of saturated fats are known to raise blood cholesterol and to increase the risk of cardiovascular diseases. It is therefore desirable to decrease the amount of saturated fats in consumer products. U.S. Pat. No. 8,153,391 and U.S. Pat. No. 8,357,503, each of which is incorporated by reference in its entirety, describe exemplary saturase enzymes that are useful in hydrolyzing saturated fatty acid residues from triacylglycerol sources to obtain low saturate oils.

In certain aspects, it is desirable to subject the hydrolyzed low saturate oil to enzymatic degumming in order to remove the phospholipids and trace metals in order to produce a desired oil with a long shelf life. It is important to recover the oils efficiently and cost effectively, particularly, when the processes are conducted on a pilot plant scale or industrial scale.

Certain emulsifiers used to facilitate the hydrolyzation process can interfere in the recovery of the low saturate oil using caustic refining at the end of hydrolyzation and/or degumming processes. Therefore, there is a need to develop a process for cost efficient production of a low saturate oil composition from a triacylglycerol source.

SUMMARY OF THE INVENTION

In certain embodiments, provided herein is a process for production of a low saturate oil composition from a triacylglycerol source comprising a) mixing a triacylglycerol source with an aqueous solution of a saturase enzyme in presence of an emulsifier to obtain an emulsion, wherein the triacylglycerol comprises at least one saturated fatty acid residue and at least one unsaturated fatty acid residue, and the emulsifier comprises an alkaline salt of an unsaturated fatty acid, b) mixing an aqueous acid with the emulsion, wherein the acid is in an amount sufficient to convert the emulsifier to a free unsaturated fatty acid and a salt, c) separating an oil phase and an aqueous phase. The mixing step a) is carried out under conditions where the saturase enzyme is active. In certain embodiments, the process further comprises fractionating the oil phase to separate the free saturated fatty acid and the low saturate oil composition.

In certain embodiments, provided herein is a process for production of a low palmitate oil composition from a triacylglycerol source comprising a) mixing a triacylglycerol source with an aqueous solution of a palmitase enzyme in presence of an emulsifier to obtain an emulsion, wherein the triacylglycerol comprises at least one palmitate fatty acid residue and at least one unsaturated fatty acid residue, and the emulsifier comprises an alkaline salt of an unsaturated fatty acid, b) mixing an aqueous acid with the emulsion, wherein the acid is in an amount sufficient to convert the emulsifier to a free unsaturated fatty acid and a salt, c) separating an oil phase and an aqueous phase. In certain embodiments, the process further comprises fractionating the oil phase to separate the free palmitate fatty acid and the low saturate oil composition.

In certain embodiments, the processes provided here further comprise an oil degumming step. In certain embodiments, the degumming step comprises water degumming, acid degumming, or enzymatic degumming. Any degumming method known to one of skill in the art can be used in the processes herein. Exemplary degumming methods are described in U.S. Pat. Nos. 4,049,686; 4,698,185; 5,239,096; 5,264,367; 5,286,886; 5,532,163; 6,001,640; 6,103,505; 6,127,137;6,143,545; 6,172,248; 6,548,633; 7,226,771; 7,312,062; 7,494,676; 7,713,727; 8,192,782; US Publication No. 2008/0182322; US Publication No. 2009/0069587; and US Publication No. 2011/0136187, each incorporated by reference in its entirety.

In one embodiment, the process for production of a low saturate oil composition from a triacylglycerol comprises a) mixing a triacylglycerol source with an aqueous solution of a saturase enzyme in presence of an emulsifier to obtain an emulsion, wherein the triacylglycerol comprises at least one saturated fatty acid residue and at least one unsaturated fatty acid residue, and the emulsifier comprises an alkaline salt of an unsaturated fatty acid, b) mixing an aqueous solution of an acid with the emulsion to obtain an acidic emulsion having a pH of less than about 4, c) mixing an aqueous solution of a base to obtain a mixture having pH of about 4-9, d) mixing a phospholipase enzyme selected from PLA1, PLA2, PLC or a combination thereof with the mixture of step c) to obtain a mixture comprising a degummed oil and an aqueous phase, e) separating the degummed oil and the aqueous phase to obtain a separated degummed oil, f) mixing the separated degummed oil with an aqueous acid solution to obtain a mixture comprising an oil phase and an aqueous phase, wherein the acid is in an amount sufficient to convert the emulsifier to a free unsaturated fatty acid and a salt, and g) separating an oil phase from the mixture of step f), wherein the oil comprises a low saturate oil composition. The mixing step a) is carried out under conditions where the saturase enzyme is active.

In certain embodiments, the separated oil is fractionated to separate the free saturated fatty acid and the low saturate oil composition.

In one embodiment, the process for production of a low palmitic oil composition comprises a) mixing a triacylglycerol source with an aqueous solution of a palmitase enzyme in presence of an emulsifier to obtain an emulsion, wherein the triacylglycerol comprises at least one palmitic fatty acid residue and at least one unsaturated fatty acid residue, and the emulsifier comprises an alkaline salt of an unsaturated fatty acid, b) mixing an aqueous solution of an acid with the emulsion to obtain an acidic emulsion having a pH of less than about 4, c) mixing an aqueous solution of a base to obtain a mixture having pH of about 4-9, d) mixing a phospholipase enzyme selected from PLA1, PLA2, PLC or a combination thereof with the mixture of step c) to obtain a mixture comprising a degummed oil and an aqueous phase, e) separating the degummed oil and the aqueous phase to obtain a separated degummed oil, f) mixing the separated degummed oil with an aqueous acid solution to obtain a mixture comprising an oil phase and an aqueous phase, wherein the acid is in an amount sufficient to convert the emulsifier to a free unsaturated fatty acid and a salt, and g) separating an oil phase from the mixture of step f), wherein the oil phase comprises a low palmitic oil composition. The mixing step a) is carried out under conditions where the palmitase enzyme is active.

In certain embodiments, the triacylglycerol source used in the processes herein is soybean oil.

Exemplary saturase enzymes, including palmitase enzymes, for use in the processes can be obtained by methods known in art, for example, methods described in U.S. Pat. Nos. 8,153,391 and 8,357,503, each incorporated by reference in its entirety.

In certain embodiments, the processes provided herein can be adapted for industrial scale production of low saturate oils.

The low saturate oils, including low palmitic oils, such as low palmitic soybean oil obtained by the processes provided here are useful in food products like bottle oil, salad dressings, mayonnaise, spreads and cooking oils.

In certain embodiments, provided herein is a low palmitic soybean oil, wherein the soybean oil contains less than about 5% palmitic acid based on total weight of the soybean oil. In certain embodiments, the low palmitic soybean oil contains about 0.5-5% palmitic acid based on total weight of the soybean oil.

BRIEF DESCRIPTION OF DRAWINGS

The FIGURE schematically illustrates an exemplary process for production of low saturate oils.

DETAILED DESCRIPTION

Definitions

As used herein, the term "saturase", refers to an enzyme that hydrolyzes saturated fatty acid esters, wherein the hydrolyzed esters may be esters of saturated fatty acids and glycerol, umbelliferol or other alcohols.

As used herein, the term "palmitase", refers to an enzyme that hydrolyzes palmitic acid, from, for example, the glycerol backbone. Exemplary saturase, including palmitase enzymes, are described in U.S. Pat. Nos. 8,153,391 and 8,357,503, each of which is incorporated by reference in its entirety.

In certain embodiments, the saturases used herein selectively hydrolyze at least 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of the saturated fatty acids. In another aspect, the palmitases used herein selectively hydrolyze fatty acids such that at least 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of the fatty acids hydrolyzed are palmitic acid. In another aspect, the stearatases used herein selectively hydrolyze fatty acids such that at least 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of the fatty acids hydrolyzed are stearic acid.

In certain embodiments, the saturase enzymes used herein selectively hydrolyze a saturated fatty acid, e.g., a palmitic acid or a stearic acid, from an Sn1, an Sn2, and/or an Sn3 position.

Examples of saturated fatty acids that can be hydrolyzed in the processes described herein include saturated fatty acids containing 2-24 carbon atoms. Exemplary acid include, but are not limited to:

Caproic: $CH_3(CH_2)_4COOH$
Caprylic: $CH_3(CH_2)_6COOH$
Capric: $CH_3(CH_2)_8COOH$
Undecanoic: $CH_3(CH_2)_9COOH$
Lauric: (dodecanoic acid): $CH_3(CH_2)_{10}COOH$
Myristic: (tetradecanoic acid): $CH_3(CH_2)_{12}COOH$
Pentadecanoic: $CH_3(CH_2)_{13}COOH$
Palmitic: (hexadecanoic acid): $CH_3(CH_2)_{14}COOH$
Margaric: $CH_3(CH_2)_{15}COOH$
Stearic (octadecanoic acid): $CH_3(CH_2)_{16}COOH$
Arachidic (eicosanoic acid): $CH_3(CH_2)_{18}COOH$
Behenic: $CH_3(CH_2)_{20}COOH$ As used herein, "low palmitic soybean oil" refers to the soybean oil obtained after treatment with a saturase enzyme in the processes described herein. In certain embodiments, the low palmitic soybean oil contains about 0.5-5% palmitic acid based on total weight of the soybean oil.

As used herein, "degummed oil" refers to an oil obtained after removal of most of the phospholipids, and lecithins (collectively known as gums) from the oil. The most commonly used processes in the industry for degumming of an oil are water degumming, acid degumming, caustic refining and enzymatic degumming. Exemplary processes are described in U.S. Pat. Nos. 4,049,686; 4,698,185; 5,239,096; 5,264,367; 5,286,886; 5,532,163; 6,001,640; 6,103,505; 6,127,137; 6,143,545; 6,172,248; 6,548,633; 7,226,771; 7,312,062; 7,494,676; 7,713,727; 8,192,782, and U.S. Publication No. 2008/0182322; U.S. Publication No. 2009/0069587; and U.S. Publication No. 2011/0136187, each of which is incorporated by reference in its entirety.

As used herein, "low saturate oil" refers to the oil obtained after removal of one or more saturated acid residues from a triacylglycerol moiety in the oil.

As used herein, "low palmitic oil" refers to the oil obtained after removal of one or more palmitic acid residues from a triacylglycerol moiety in the oil.

As used herein, "phospholipases" refer to enzymes exhibiting activity with phospholipids. As described in, for example, U.S. Publication No. 2009/0069587, the types of phospholipases are based on the position on the phospholipid molecule at which the enzyme reacts, and are known as PLC, PLD and PLA, including PLA1 and PLA2. In certain embodiments, PLA enzymes include acyltransferases, including but not limited to those described in U.S. Pat. No. 8.192.782 and U.S. Publication No. 2011/0136187.

In certain embodiments, provided herein is a process for production of a low saturate oil composition comprising a) mixing a triacylglycerol source with an aqueous solution of a saturase enzyme in presence of an emulsifier to obtain an emulsion, wherein the triacylglycerol comprises at least one saturated fatty acid residue and at least one unsaturated fatty acid residue, and the emulsifier comprises an alkaline salt of an unsaturated fatty acid, b) mixing an aqueous acid with the emulsion, wherein the acid is in an amount sufficient to convert the emulsifier to a free unsaturated fatty acid and a salt, c) separating an oil phase and an aqueous phase. In certain embodiments, the process further comprises fractionating the oil phase to separate the free saturated fatty acid and the low saturate oil composition. The mixing step a) is carried out under reaction conditions where the saturase enzyme is active. Such reaction conditions, including pH and temperature conditions are known to one of skill in the art.

In certain embodiments, provided herein is a process for production of a low palmitic oil composition comprising a) mixing a triacylglycerol source with an aqueous solution of a palmitase enzyme in presence of an emulsifier to obtain an emulsion, wherein the triacylglycerol comprises at least one palmitic acid residue and at least one unsaturated fatty acid residue, and the emulsifier comprises an alkaline salt of an unsaturated fatty acid, b) mixing an aqueous acid with the emulsion, wherein the acid is in an amount sufficient to convert the emulsifier to a free unsaturated fatty acid and a salt, c) separating an oil phase and an aqueous phase. In certain embodiments, the process further comprises fractionating the oil phase to separate palmitic acid and the low palmitic oil composition.

In one embodiment, the process for production of a low saturate oil composition comprises a) mixing a triacylglycerol source with an aqueous solution of a saturase enzyme in presence of an emulsifier to obtain an emulsion, wherein the triacylglycerol comprises at least one saturated fatty acid residue and at least one unsaturated fatty acid residue, and the emulsifier comprises an alkaline salt of an unsaturated fatty acid, b) mixing an aqueous solution of an acid with the emulsion to obtain an acidic emulsion having a pH of less than about 4, c) mixing an aqueous solution of a base to obtain a mixture having pH of about 4-9, d) mixing a phospholipase enzyme selected from PLA1, PLA2, PLC and a combination thereof with the mixture of step c) to obtain a mixture comprising a degummed oil and an aqueous phase, e) separating the degummed oil and the aqueous phase to obtain a separated degummed oil, f) mixing the separated degummed oil with an aqueous acid solution to obtain a mixture comprising an oil phase and an aqueous phase, wherein the acid is in an amount sufficient to convert the emulsifier to a free unsaturated fatty acid and a salt, and g) separating the oil phase from the mixture of step f), wherein the oil phase comprises a low saturate oil composition.

In one embodiment, the process for production of a low palmitic oil composition comprises a) mixing a triacylglycerol source with an aqueous solution of a palmitase enzyme in presence of an emulsifier to obtain an emulsion, wherein the triacylglycerol comprises at least one palmitic fatty acid residue and at least one unsaturated fatty acid residue, and the emulsifier comprises an alkaline salt of an unsaturated fatty acid, b) mixing an aqueous solution of an acid with the emulsion to obtain an acidic emulsion having a pH of less than about 4, c) mixing an aqueous solution of a base to obtain a mixture having pH of about 4-9, d) mixing a phospholipase enzyme selected from PLA1, PLA2, PLC and a combination thereof with the mixture of step c) to obtain a mixture comprising a degummed oil and an aqueous phase, e) separating the degummed oil and the aqueous phase to obtain a separated degummed oil, f) mixing the separated degummed oil with an aqueous acid solution to obtain a mixture comprising an oil phase and an aqueous phase, wherein the acid is in an amount sufficient to convert the emulsifier to a free unsaturated fatty acid and a salt, and g) separating the oil phase from the mixture of step f), wherein the oil phase comprises a low palmitic oil composition. In certain embodiments, the separated oil phase is fractionated to separate palmitic acid and the low palmitic oil composition.

In certain embodiments, the processes provided herein can be adapted for industrial scale production of low saturate oils.

In certain embodiments, the amount of acid in step b) is sufficient to obtain pH of about 1-4, 2-4 or 3-4. In certain embodiments, the amount of base in step c) is sufficient to obtain pH of about 4-6.5, 5.5-7, 7-8, or 8-9.

In certain embodiments, the separated oil phase is cooled to −20 to 20° C., −15 to 15° C., −10 to 10° C., −5 to 5° C., or 0 to 5° C. to solidify the saturated fatty acid, including palmitic acid. The solidified saturated fatty acid is separated by methods known to in the art to obtain the low saturate oil composition.

The triacylglycerol sources that can be used in the methods provided herein include, but are not limited to, any algal oil, vegetable oil, or an animal fat or oil, e.g., *Neochloris oleoabundans* oil, *Scenedesmus dimorphus* oil, *Euglena gracilis* oil, *Phaeodactylum tricornmutum* oil, *Pleurochrysis camerae* oil, *Prymnesium parvum* oil, *Tetraselmis chui* oil, *Tetraselmis suecica* oil, *Isochrysis galbana* oil, *Nannochloropsis salina* oil, *Botryococcus braunii* oil, *Dunaliella tertiolecta* oil, *Nannochloris* species oil, *Spirulina* species oil, Chlorophycease (green algae) oil, and Bacilliarophy oil, canola oil, castor oil, coconut oil, coriander oil, corn oil, cottonseed oil, hazelnut oil, hempseed oil, linseed oil, meadowfoam oil, olive oil, palm oil, palm kernel oil, peanut oil, rapeseed oil, rice bran oil, safflower oil, sasanqua oil, soybean oil, sunflower seed oil, tall oil tsubaki oil, varieties of natural oils having altered fatty acid compositions via Genetically Modified Organisms (GMO) or traditional genetic breeding such as high oleic, low linolenic, or low saturate oils (high oleic canola oil, low linolenic soybean oil or high stearic sunflower oils); animal fats (tallow, lard, butter fat, and chicken fat), fish oils (candlefish oil, cod-liver oil, orange roughy oil, sardine oil, herring oil, and menhaden oil), or blends of any one of the above. In one embodiment, the triacylglycerol source in the processes herein is soybean oil. In another embodiment, the triacylglycerol sources in the processes herein are crude non-degummed or semi-processed oils, including crude non-degummed or semi-processed soybean oils (degummed, chemically refined, bleached, and/or deodorized where lecithin is added).

The emulsifiers used in the processes herein comprise alkaline salts of unsaturated fatty acids. Any alkaline salt of an unsaturated fatty acid known to one of skill in the art can be used in the processes described herein. In certain embodiments, the emulsifier is an alkaline salt of a long chain unsaturated fatty acids. In certain embodiments, the emulsifier has HLB greater than 12, 14, 16, or 18. In certain embodiments, the emulsifier has HLB of 12-18, 12-16, 12-14, 14-18, 14-16 or 16-18. In certain embodiments, the emulsifier has HLB 12, 14, 16, or 18. In certain embodiments, the emulsifier is selected from sodium oleate, potassium oleate, sodium linoleate, potassium linoleate, sodium linolenate, potassium linolenate or a combination thereof. In one embodiment, the emulsifier is selected from potassium oleate and sodium oleate.

In certain embodiments, the amount of emulsifier used in the processes herein is about 1-10%, 2-8%, 2-6%, 2-5% or 3-5% based on the total weight of the oil. In one embodiment, the amount of emulsifier used is about 1, 3, 5, 7, or 10% based on the total weight of the oil.

In certain embodiments, the mixing in step a) comprises shear mixing to obtain the emulsion. In certain embodiments, the oil or fat is mixed with the emulsifier prior to addition of the saturase enzyme. In certain embodiments, the mixture of oil/fat and emulsifier is homogenized before and/or after addition of the enzyme to ensure uniform emulsion.

In one embodiment, the shear mixing is conducted for about 5-30 minutes, about 5-20 minutes, about 5-15 minutes, about 7-15 minutes, about 7-12 minutes or about 10 minutes with a shear mixer, such as an Ultra Turrax® T-50. In another embodiment, the shear mixing is conducted in an inline shear mixer such as a DISPAX REACTOR for less than about 1 minute.

In certain embodiments, the reaction mixture of step a) comprises about 1 to 30% water based on the total weight of the reactants. In certain embodiments, the reaction mixture of step a) comprises about 1 to 20%, 1-15%, 1-10%, 1-5%, 5-25%, or 10-25% water based on the total weight of the reactants. In one embodiment, the reaction mixture comprises about 1, 3, 5, 7, 10, 15, 17 or 20% water based on the total weight of the reactants.

In certain embodiments, the process provided herein reduces the saturate content, including, the palmitate content of the oil/fat to about 15% or less, 10% or less, or 5% or less based on the total weight of the oil/fat. In certain embodiments, the saturate content, including, the palmitate content of the oil/fat is reduced to about 10, 7, 5, 4, 3, 2, 1% or less based on the total weight of the oil/fat. In certain embodiments, the process provided herein reduces the saturate content, including, the palmitate content of the oil/fat to about 0.5-20%, 3-15%, 3-10%, 3-7%, 3-5%, 2-10%, 2-7%, 2-5%, 1-15%, 1-12%, 1-10%, 1-8%, 1-7% or 1- 5%, 1-3%, 0.5-7%, 0.5-5%, 0.5-3%, or less.

In the processes provided herein, any acids suitable for use in a food product can be used. Exemplary acids include, but are not limited to phosphoric acid, acetic acid, citric acid, tartaric acid, succinic acid, and a mixture thereof. In one embodiment, the acid is citric acid. Exemplary bases for use herein include, but are not limited to sodium hydroxide and potassium hydroxide.

In one embodiment, the saturase enzyme, including the palmitase enzyme, is added in one portion. In one embodiment, the saturase enzyme, including the palmitase enzyme, is added in multiple portions. In one embodiment, the saturase enzyme, including the palmitase enzyme, is added to the triacylglycerol source at a temperature from about 15 to 50° C., about 20 to 40° C., about 22 to 30° C. or about 22 to 25° C.

In certain embodiments, the processes provided herein further comprise an oil degumming step that comprises water degumming, acid degumming, or enzymatic degumming. Any degumming method known to one of skill in the art can be used in the processes herein. Exemplary degumming methods are described in U.S. Pat. Nos. 4,049,686; 4698,185; 5,264,367; 5,532,163; 6,001,640; 6,103,505; 6,127,137; 6,143,545; 6,172,248; 6,548,633; 7,713,727; 7,226,771; 7,312,062; 7,494,676; 8,192,782; US Publication No. 2008/0188322; US Publication No. 2009/0069587; US Publication No. 2011/0136187, each incorporated by reference in its entirety.

The amounts of saturase, palmitase, PLA and PLC enzymes used in the processes provided herein depend on the reaction conditions, the type of oil and the type of enzyme used. In certain embodiments, the amount of enzyme used is in the range from 10 to 20,000 units, from 20 to 10,000 units, from 50 to 5,000 units, or from 100 to 2,000 units, per 1 kg of the oil.

In one embodiment, the process for production of a low palmitic oil composition comprises a) mixing a triacylglycerol source with an aqueous solution of a palmitase enzyme in presence of potassium oleate to obtain an emulsion, wherein the triacylglycerol comprises at least one palmitic acid residue and at least one unsaturated fatty acid residue, b) mixing an aqueous solution of citric acid to adjust the pH to less than about 4, in one embodiment, less than about 2, c) mixing an aqueous solution of sodium hydroxide to obtain a mixture having pH of about 4-9, in one embodiment, about 4.5-7, d) mixing a phospholipase enzyme selected from PLA1, PLA2, PLC and a combination of either PLAs and PLC to obtain a mixture comprising a degummed oil and an aqueous phase, e) separating the degummed oil and the aqueous phase, f) mixing the degummed oil with an aqueous citric acid solution to obtain a mixture comprising an oil phase and an aqueous phase, wherein the citric acid is in an amount sufficient to convert potassium oleate in the oil to a free oleic acid and potassium citrate salt, and g) separating the oil phase comprising a low palmitic oil composition, palmitic acid and free oleic acid. In certain embodiments, the separated oil phase is fractionated to separate the palmitic acid and the low palmitic oil composition.

In certain embodiments, the separated oil phase is cooled to 0-5° C. to solidify palmitic acid. The solidified palmitic acid is separated to obtain the low palmitic oil composition.

In certain embodiments, the low saturate oil composition is subjected to further processing steps known in the art including bleaching or deodorizing, as may be necessary or desirable depending on the end use for which the oil composition is intended.

Exemplary Processes

An Exemplary process is illustrated in a flow diagram in the FIGURE.

In an exemplary process, about 1000 kg of crude soybean oil is used. The oil is heated to about 70° C. and mixed to homogenize with a tank agitator. If crude non-degummed oil is used as a starting material, no lecithin is added to the oil. If other sources of oil are used, including a degummed oil, up to about 50 kg of soybean lecithin (0 to 5% w/w oil) at about 70° C. is added and a uniform mixture is formed with a tank agitator. The oil is cooled to about 20 to 50° C. About 50 kg of palmitase formulated enzyme is pumped through a mass flow meter into the oil. About 10 to 50 kg of water (1 to 5 percent w/w oil) is pumped through a mass flow meter into the oil. The oil is pumped through a high shear mixer producing a water-in-oil mechanical emulsion into Reaction Tank 1. The oil is mixed for about 24 to 48 hours at a temperature from about 20 to 50° C. About 30 to 50 kg potassium oleate (3 to 5 percent w/w oil) emulsifier is added and mixed. About 50 kg of palmitase formulated enzyme is pumped through a mass flow meter into the oil. The oil will be pumped through a second high shear mixer producing a water-in-oil mechanical emulsion into Reaction Tank 2.

The oil is mixed for about 24 to 72 hours at a temperature from about 25 to 40° C. About 50 parts per million of Lecitase® Ultra (PLA1) (0.005 percent w/w oil) and/or about 200 parts per million of Purifine® PLC (0.02 percent w/w oil) is added to the oil. The oil is mixed for about 1 to 4 hours. The oil is pumped through a heat exchanger to about 85° C., where it is then centrifuged. The lighter phase of oil containing the cleaved palmitic acid and potassium oleate (1030 to 1050 kg) is separated from the heavy phase comprising wet gums and denatured protein (130 to 200 kg).

The oil layer is cooled to about 0 to 5° C. and slowly agitated for about 24 hours. The palmitic fatty acid is allowed to solidify enabling the fractionation of palmitic acid. Optionally, about 1 to 10 kg (0.1 to 1 percent w/w oil) of diatomaceous earth is added to aid in filtration of the treated oil. The filtrate comprises the low palmitic oil and potassium oleate (857 to 1008 kg) is separated from the precipitate comprising palmitic acid and diatomaceous earth (40 to 160 kg). The precipitate is heated to about 100° C., and filtered to obtain a filtrate comprising palmitic acid (37 to 137 kg).

The material retained on the filter comprising diatomaceous earth (1.3 to 13 kg) is collected.

Processing of Palmitase Treated Oil:

Soap to Acid Conversion:

The filtrate comprising the low palmitic oil and potassium oleate, described above, is heated to about 50 to 70° C. in an agitated tank. About 50% solution of citric acid is pumped into the oil in order to convert the potassium oleate soaps into oleic acid (12 to 20 kg of 50 percent w/w). In certain embodiments, the treatment with acid to convert the potassium soaps to fatty acid may optionally occur immediately following the centrifugation step described above, prior to the cooling and separation of the palmitic fatty acids.

Bleaching:

The oil is heated to about 60° C. in a stirred tank, where about 1 to 5 kg acid activated bleaching earth (Tonsil Optimum FF or equivalent) is added as slurry. A vacuum of approximately 100 mBar is applied and the oil is heated to about 90 to 120° C. for approximately 30 minutes. The oil is filtered to obtain an oil fraction containing low palmitic oil and oleic fatty acids (851 to 1007 kg), and a solid fraction containing spent bleaching earth (1.3 to 6.5 kg). In certain embodiments, the removal of the palmitic fatty acid may occur after the bleaching process prior to the deodorization step.

Deodorization:

The oil fraction is heated up to about 250° C. under 0.5 to 3 mBar where about 0.1 to 3% (w/w oil) steam is added for about 30 to 180 minutes. The oil is cooled to about 100° C. where about 1 to 25 ppm of 50% citric acid is added in order to chelate any trace metals. The vacuum is broken with nitrogen to prevent the oil exposure to air. Upon discharging the oil from the vacuum equipment, the oil is filtered through a 5 micron bag to remove the chelated metals. The oil is stored under nitrogen blanketing.

The refined, bleached and deodorized low palmitic oil (786 to 967.7 kg) and a deodorizer distillate containing oleic fatty acid (39 to 65 kg) are obtained from the process. The distillate may be treated with about 50 percent solution of KOH to form potassium oleate to be reused in the process (10 to 20 kg).

Exemplary Enzymes Used in the Process

Exemplary saturase, including palmitase enzymes, and methods of obtaining the enzymes are described in U.S. Pat. No. 8,153,391 and U.S. Pat. No. 8,357,503, each of which is incorporated by reference in its entirety.

Exemplary enzymes comprise a polypeptide selected from the group consisting of isolated, synthetic and recombinant polypeptides having a saturase, including, palmitase activity, wherein the polypeptide either
  i) is encoded by a nucleic acid comprising a nucleic acid sequence having at least 85% sequence identity to SEQ ID NO:1 and has one, two, three, four, five, six, seven, eight, nine, ten, eleven or twelve or more, or all the base residue changes recited in Table A, Table B, or Table C below, wherein the nucleic acid encodes at least one polypeptide having a saturase, including palmitase activity,

TABLE A

| amino acid residue position | original amino acid | new amino acid | original codon | new codon |
|---|---|---|---|---|
| 7 | Y | L | TAC | CTT |
| 15 | A | L | GCC | CTG |
| 15 | A | M | GCC | ATG |
| 16 | D | W | GAT | TGG |
| 31 | M | I | ATG | ATT |
| 32 | G | E | GGC | GAG |
| 32 | G | P | GGC | CCT |
| 34 | L | M | CTG | ATG |
| 43 | L | I | CTG | ATT |
| 46 | F | F | TTC | TTT |
| 48 | A | C | GCC | TGT |
| 48 | A | M | GCC | ATG |
| 48 | A | T | GCC | ACT |
| 49 | D | N | GAC | AAT |
| 49 | D | R | GAC | CGT |
| 49 | D | S | GAC | TCT |
| 52 | A | M | GCC | ATG |
| 68 | S | F | TCG | TTT |
| 68 | S | Y | TCG | TAT |
| 85 | R | A | CGG | GCT |
| 85 | R | D | CGG | GAT |
| 85 | R | Q | CGG | CAG |
| 85 | R | S | CGG | TCT |
| 85 | R | T | CGG | ACG |
| 85 | R | Y | CGG | TAT |
| 95 | E | K | GAG | AAG |
| 92 | A | V | GCG | GTT |
| 92 | A | E | GCG | GAG |
| 95 | E | D | GAG | GAT |
| 95 | E | A | GAG | GCT |
| 96 | A | K | GCG | AAG |
| 96 | A | R | GCG | AGG |
| 97 | A | S | GCC | TCG |
| 101 | K | R | AAG | CGT |
| 104 | V | L | GTG | TTG |
| 113 | Y | L | TAT | CTT |
| 116 | E | A | GAG | GCG |
| 116 | E | C | GAG | TGT |
| 116 | E | D | GAG | GAT |
| 116 | E | F | GAG | TTT |
| 116 | E | I | GAG | ATT |
| 116 | E | I | GAG | ATT |
| 116 | E | L | GAG | CTT |
| 116 | E | N | GAG | AAT |
| 116 | E | Q | GAG | CAG |
| 116 | E | S | GAG | AGT |
| 116 | E | T | GAG | ACT |
| 116 | E | V | GAG | GTT |
| 116 | E | W | GAG | TGG |
| 116 | E | Y | GAG | TAT |
| 117 | L | M | CTG | ATG |
| 120 | K | R | AAG | AGG |
| 133 | S | A | AGT | GCT |
| 136 | A | S | GCG | TCG |
| 137 | G | F | GGC | TTT |
| 139 | L | M | CTC | ATG |
| 140 | H | R | CAC | AGG |
| 142 | N | W | AAC | TGG |
| 144 | A | I | GCG | ATT |
| 144 | A | L | GCG | TTG |
| 144 | A | M | GCG | ATG |
| 144 | A | V | GCG | GTG |
| 149 | E | H | GAG | CAT |
| 150 | A | I | GCG | ATT |
| 150 | A | M | GCG | ATG |
| 150 | A | W | GCG | TGG |
| 153 | S | N | AGC | AAT |
| 153 | S | G | AGC | GGT |
| 158 | N | D | AAC | GAC |
| 162 | P | G | CCG | GGT |
| 162 | P | K | CCG | AAG |
| 162 | P | S | CCG | TCG |

TABLE A-continued

| amino acid residue position | original amino acid | new amino acid | original codon | new codon |
|---|---|---|---|---|
| 162 | P | S | CCG | TCG |
| 162 | P | S | CCG | TCG |
| 183 | V | I | GTG | ATT |
| 166 | Q | A | CAG | GCG |
| 166 | Q | E | CAG | GAG |
| 166 | Q | T | CAG | ACG |
| 167 | I | F | ATT | TTT |
| 167 | I | K | ATT | AAG |
| 167 | I | L | ATT | CTG |
| 167 | I | R | ATT | CGT |
| 167 | I | Y | ATT | TAT |
| 172 | R | H | CGC | CAT |
| 172 | R | K | CGC | AAG |
| 172 | R | L | CGC | CTT |
| 172 | R | Y | CGC | TAT |
| 180 | L | K | CTC | AAG |
| 180 | L | R | CTC | AGG |
| 185 | A | C | GCG | TGT |
| 185 | A | N | GCG | AAT |
| 190 | E | A | GAA | GCG |
| 190 | E | K | GAA | AAG |
| 190 | E | M | GAA | ATG |
| 190 | E | Q | GAA | CAG |
| 190 | E | R | GAA | AGG |
| 200 | L | I | CTA | ATT |

TABLE A-continued

| amino acid residue position | original amino acid | new amino acid | original codon | new codon |
|---|---|---|---|---|
| 200 | L | V | CTA | GTA |
| 200 | L | V | CTA | GTT |
| 201 | E | Y | GAG | TAT |
| 203 | A | H | GCG | CAT |
| 203 | A | P | GCG | CCG |
| 203 | A | R | GCG | AGG |
| 207 | M | L | ATG | CTT |
| 214 | T | H | ACC | CAT |
| 214 | T | K | ACC | AAG |
| 214 | T | R | ACC | AGG |
| 214 | T | S | ACC | TCG |
| 214 | T | V | ACC | GTT |
| 215 | G | A | GGG | GCG |
| 222 | L | I | CTG | ATT |
| 225 | A | S | GCG | TCT |
| 163 | R | Y | CGG | TAT |
| 163 | R | M | CGG | ATG |
| 163 | R | T | CGG | ACG |
| 163 | R | L | CGG | TTG |
| 163 | R | C | CGG | TGT |
| 95 | E | K | | |
| 163 | R | F | | |
| 183 | V | I | | |

TABLE B

| old codon | new codon | AA # | old codon | new codon | AA # | old codon | new codon | AA # | old codon | new codon | AA # | old codon | new codon | AA # | old codon | new codon | AA # |
|---|---|---|---|---|---|---|---|---|---|---|---|---|---|---|---|---|---|
| GCG | GCT | 35 | AGC | AGT | 108 | GTG | GTT | 183 | ACC | ACG | 188 | | | | | | |
| GCG | GCT | 35 | GTG | GTT | 102 | AGC | AGT | 108 | CTG | TTG | 124 | GTC | GTG | 128 | AGT | TCT | 133 |
| GCG | GCT | 35 | ACC | ACG | 188 | | | | | | | | | | | | |
| GCG | GCT | 35 | GTG | GTT | 183 | ACC | ACG | 188 | | | | | | | | | |
| GCG | GCT | 35 | GTG | GTT | 102 | AGC | AGT | 108 | GTC | GTG | 128 | | | | | | |
| GCG | GCT | 35 | GTG | GTT | 102 | AGC | AGT | 108 | CTG | TTG | 124 | GTC | GTG | 128 | AGT | TCT | 133 |
| | | | GCG | GCT | 35 | GTG | GTT | 102 | CTG | TTG | 124 | GTC | GTG | 128 | | | |
| GCG | GCT | 35 | GTG | GTT | 183 | | | | | | | | | | | | |
| GCG | GCT | 35 | GTC | GTG | 128 | AGT | TCT | 133 | | | | | | | | | |
| GCG | GCT | 35 | AGT | TCT | 133 | GTG | GTT | 183 | ACC | ACG | 188 | | | | | | |
| GCG | GCT | 35 | AGC | AGT | 108 | CTG | TTG | 124 | AGT | TCT | 133 | GTG | GTT | 183 | ACC | ACG | 188 |
| GCG | GCT | 35 | GGC | GGA | 45 | GTG | GTT | 102 | AGC | AGT | 108 | CTG | CTT | 117 | CGG | AGG | 126 |
| GCG | GCT | 35 | GGC | GGA | 45 | CTG | CTT | 117 | CTG | TTG | 124 | | | | GTG | GTT | 183 |
| GCG | GCT | 35 | GGC | GGA | 45 | AGC | AGT | 108 | CTG | CTT | 117 | CGG | AGG | 126 | ACC | ACG | 188 |
| GGC | GGA | 45 | GTG | GTT | 102 | CTG | CTT | 117 | GTC | GTG | 128 | AGT | TCT | 133 | | | |
| | | | GCG | GGA | 45 | GTG | GTT | 102 | AGC | AGT | 108 | CTG | CTT | 117 | CGG | AGG | 126 |
| GGC | GGA | 45 | GTG | GTT | 102 | CTG | CTT | 117 | | | | | | | | | |
| GCG | GCT | 35 | GGC | GGA | 45 | AGC | AGT | 108 | CTG | CTT | 117 | ACC | ACG | 188 | | | |
| GCG | GCT | 35 | GGC | GGA | 45 | CTG | CTT | 117 | CTG | TTG | 124 | GTC | GTG | 128 | AGT | TCT | 133 |
| GCG | GCT | 35 | GGC | GGA | 45 | AGC | AGT | 108 | CTG | CTT | 117 | CTG | TTG | 124 | AGT | TCT | 133 |
| GCG | GCT | 35 | GGC | GGA | 45 | AGC | AGT | 108 | CTG | CTT | 117 | AGT | TCT | 133 | ACC | ACG | 188 |
| GCG | GCT | 35 | GGC | GGA | 45 | GTG | GTT | 102 | CTG | CTT | 117 | CTG | TTG | 124 | CGG | AGG | 126 |
| GGC | GGA | 45 | | | | AGC | AGT | 108 | CTG | CTT | 117 | ACC | ACG | 188 | | | |
| GCG | GCT | 35 | GGC | GGA | 45 | CTG | CTT | 117 | ACC | ACG | 188 | | | | | | |
| GCG | GCT | 35 | GGC | GGA | 45 | AGC | AGT | 108 | CGG | AGG | 126 | GTC | GTG | 128 | AGT | TCT | 133 |
| GCG | GCT | 35 | GGC | GGA | 45 | AGC | AGT | 108 | AGT | TCT | 133 | | | | | | |
| GCG | GCT | 35 | GGC | GGA | 45 | | | | | | | | | | | | |
| GCG | GCT | 35 | GGC | GGA | 45 | CTG | TTG | 90 | GTG | GTT | 183 | | | | | | |
| GCG | GCT | 35 | GGC | GGA | 45 | AGC | AGT | 108 | GTC | GTG | 128 | AGT | TCT | 133 | | | |
| GCG | GCT | 35 | GGC | GGA | 45 | GTG | GTT | 102 | GTC | GTG | 128 | GTG | GTT | 183 | ACC | ACG | 188 |
| GCG | GCT | 35 | GGC | GGA | 45 | GTG | GTT | 102 | AGC | AGT | 108 | CGG | AGG | 126 | GTC | GTG | 128 |
| GCG | GCT | 35 | CTG | CTT | 117 | ACC | ACG | 188 | | | | | | | | | |
| GCG | GCT | 35 | CTG | CTT | 117 | GTG | GTT | 183 | ACC | ACG | 188 | | | | | | |
| GCG | GCT | 35 | AGC | AGT | 108 | CTG | CTT | 117 | CTG | TTG | 124 | GTC | GTG | 128 | AGC | AGT | 153 |
| GCG | GCT | 35 | GTG | GTT | 102 | AGC | AGT | 108 | CTG | CTT | 117 | CGG | AGG | 126 | AGT | TCT | 133 |
| GTG | GTT | 102 | AGC | AGT | 108 | CTG | CTT | 117 | CGG | AGG | 126 | | | | | | |
| GCG | GCT | 35 | GTG | GTT | 102 | CTG | CTT | 117 | GTG | GTT | 183 | ACC | ACG | 188 | | | |
| GCG | GCT | 35 | GTG | GTT | 102 | CTG | CTT | 117 | CTG | TTG | 124 | GTG | GTT | 183 | ACC | ACG | 188 |
| GCG | GCT | 35 | AGC | AGT | 108 | CTG | CTT | 117 | GTC | GTG | 128 | AGT | TCT | 133 | GTG | GTT | 183 |
| GCG | GCT | 35 | CTG | CTT | 117 | CTG | TTG | 124 | AGT | TCT | 133 | | | | | | |
| CTG | CTT | 117 | CGG | AGG | 126 | AGT | TCT | 133 | CGC | CAC | 172 | ACC | ACG | 188 | | | |
| AGC | AGT | 108 | CTG | CTT | 117 | GTG | GTT | 183 | ACC | ACG | 188 | | | | | | |
| AGC | AGT | 108 | CTG | CTT | 117 | CTG | TTG | 124 | CGG | AGG | 126 | GTC | GTG | 128 | GTG | GTT | 183 |

TABLE B-continued

| | | | | | | | | | | | | | | |
|---|---|---|---|---|---|---|---|---|---|---|---|---|---|---|
| | | | GCG | GCT | 35 | CTG | CTT | 117 | ACC | ACG | 188 | | | |
| GCG | GCT | 35 | CTG | CTT | 117 | GTG | GTT | 183 | | | | | | |
| GCG | GCT | 35 | GTG | GTT | 102 | CTG | CTT | 117 | AGT | TCT | 133 | GTG | GTT | 183 | ACC | ACG | 188 |

| old codon | new codon | AA # | old codon | new codon | AA # | old codon | new codon | AA # |
|---|---|---|---|---|---|---|---|---|
| | | | GTG | GTT | 183 | | | |
| GTG | GTT | 183 | | | | | | |
| AGT | TCT | 133 | | | | | | |
| ACC | ACG | 188 | | | | | | |
| ACC | ACG | 188 | | | | | | |
| GTC | GTG | 128 | | | | | | |
| AGT | TCT | 133 | GTG | GTT | 183 | ACC | ACG | 188 |
| ACC | ACG | 188 | | | | | | |
| CC | ACG | 188 | | | | | | |
| ACC | ACG | 188 | | | | | | |
| ACC | ACG | 188 | | | | | | |

TABLE C

| old codon | new codon | old AA | new AA | AA # |
|---|---|---|---|---|
| CCG | TCG | P | S | 162 |
| ACG | ATG | T | M | 22 |
| AGC | GGC | S | G | 153 |
| GAA | AAA | E | K | 190 |
| CGC | CAC | R | H | 172 |
| ATG | ATA | M | I | 31 |
| GTG | ATG | V | M | 83 |
| CTA | ATA | L | I | 200 |
| GCA | GTA | A | V | 211 |
| ACG | ATG | T | M | 22 | or ii) has at least 85% sequence identity to SEQ ID NO:2 over a region of at least about 100 residues, and having one, two, three, four, five, six, seven, eight, nine, ten, eleven or twelve or more or all the amino acid residue changes recited in Table A, or Table C above, or iii) comprises an amino acid sequence of SEQ ID NO:2 but also comprising at least one of amino acid residue modification D61A; D61E; R72E; R72K; E116A; E116Q; E116R; E116T; E116V; S133A; I151G; I151A; V163R; D164R, or a combination thereof, or iv) comprises an amino acid sequence of SEQ ID NO:2 but also comprising at least one of amino acid residue modification 120L; V62S; G77P; V83C; D88H; Y113G; E116T; E116G; H140K; K146S; I167S; L180E; E194M; A211Q; S212Y; G215C; G215V; G215W; A218H; A218S; V223A; A225M; A225Q, or a combination thereof, or v) comprises an amino acid sequence of SEQ ID NO:2 but also comprising the following amino acid residue modifications D61E; R72K; V83M, R85Y, V163R and R172H.

In certain embodiments, the polypeptide sequence used herein is encoded by a nucleic acid comprising a nucleic acid sequence having at least 85%, 98%, 90%, 95% sequence identity to SEQ ID NO:1, and has one, two, three, four, five, six, seven, eight, nine, ten, eleven or twelve or more, or all the base residue changes recited in Table A, Table B, or Table C.

In certain embodiments, the polypeptide sequence used herein has at least 85%, 88%, 90%, 95% sequence identity to SEQ ID NO:2, and has one, two, three, four, five, six, seven, eight, nine, ten, eleven or twelve or more, or all the amino acid residue changes recited in Table A, Table B, or Table C.

The nucleic acid and polypeptide sequences referred above are as follows:

```
SEQ ID NO: 1
atgctgaaaccgcctccctacggacgcctgctgcgcgaactggccgatatcccggccatcgtgacggcaccgttccggggcg ctgcgaaaatgggcaaactggcggatggcgagccggtactggtgctgcccggcttcctggccgacgacaacgccacctcggt gctgcgcaagaccttcgatgtcgcgggctttgcctgttcgggctgggaacgcggcttcaacctcggcattcgtggcgacctcgt ggaccggctggtcgaccggctgcgggcggtgtcggaggcggccggtggtcagaaggtgatcgtggtcggctggagcctcg gcggcctctatgcgcgcgagctgggccacaaggcgcccgaactgatccggatggtcgtcacgctcggcagtccgttcgcggg cgacctccacgccaaccatgcgtggaagatctacgaggcgatcaacagccacacggtcgacaacctgccgatcccggtcgatt tccagattaagccgccggtgcgcaccatcgcggtgtggtcgccgctcgacggggtggtggcgccggagacctcggaaggct cgcccgagcagtcggacgagcggctagagctggcggtgacccacatgggctttgccgcatcgaagaccggggccgaggct gtggtccggctggtcgcggcgcggctctag
```

SEQ ID NO: 2 (encoded by SEQ ID NO: 1):
1-letter code:
MLKPPPYGRLLRELADIPAIVTAPFRGAAKMGKLADGEPVLVLPGFLADDNATS

VLRKTFDVAGFACSGWERGFNLGIRGDLVDRLVDRLRAVSEAAGGQKVIVVGW

SLGGLYARELGHKAPELIRMVVTLGSPFAGDLHANHAWKIYEAINSHTVDNLPIP

VDFQIKPPVRTIAVWSPLDGVVAPETSEGSPEQSDERLELAVTHMGFAASKTGAE

AVVRLVAARL- 3-letter code:
Met Leu Lys Pro Pro Pro Tyr Gly Arg Leu Leu Arg Glu Leu Ala Asp
Ile Pro Ala Ile Val Thr Ala Pro Phe Arg Gly Ala Ala Lys Met Gly
Lys Leu Ala Asp Gly Glu Pro Val Leu Val Leu Pro Gly Phe Leu Ala
Asp Asp Asn Ala Thr Ser Val Leu Arg Lys Thr Phe Asp Val Ala Gly
Phe Ala Cys Ser Gly Trp Glu Arg Gly Phe Asn Leu Gly Ile Arg Gly
Asp Leu Val Asp Arg Leu Val Asp Arg Leu Arg Ala Val Ser Glu Ala
Ala Gly Gly Gln Lys Val Ile Val Val Gly Trp Ser Leu Gly Gly Leu
Tyr Ala Arg Glu Leu Gly His Lys Ala Pro Glu Leu Ile Arg Met Val
Val Thr Leu Gly Ser Pro Phe Ala Gly Asp Leu His Ala Asn His Ala
Trp Lys Ile Tyr Glu Ala Ile Asn Ser His Thr Val Asp Asn Leu Pro
Ile Pro Val Asp Phe Gln Ile Lys Pro Pro Val Arg Thr Ile Ala Val
Trp Ser Pro Leu Asp Gly Val Val Ala Pro Glu Thr Ser Glu Gly Ser
Pro Glu Gln Ser Asp Glu Arg Leu Glu Leu Ala Val Thr His Met Gly
Phe Ala Ala Ser Lys Thr Gly Ala Glu Ala Val Val Arg Leu Val Ala
Ala Arg Leu

SEQ ID NO: 3:
ATGCTCAAGCCCCCACCTTACGGCCGTCTGCTCCGCGAACTGGCTGATATCCCGG

CGATCGTGACTGCTCCGTTCCGCGGCGCAGCCAAAATGGGCAAACTGGCTGATGG

CGAGCCGGTACTGGTGCTGCCCGGCTTCCTGGCGGACGACAACGCGACCAGCGT

GCTGCGGAAGACCTTCGAGGTCGCCGGCTTTGCGTGCAGCGGCTGGGAAAAGGG

CTTCAACCTCGGCATTCGTGGCGACCTCATGGACTACCTGGTCGACCGCCTGCGC

GCCGTGAGCGAGGCCGCGGGGGGGCAGAAGGTTATCGTGGTCGGCTGGAGTCT

CGGCGGCCTCTACGCCCGGGAGCTTGGCCACAAGGCCCCCGAACTGATCAGGAT

GGTCGTCACGCTCGGCTCTCCGTTCGCCGGCGACCTCCACGCGAACCATGCCTG

GAAGATCTACGAGGCCATCAACTCCCACACGGTCGACAACCTGCCGATCCCGCGC

GATTTCCAGATTAAGCCGCCGGTGCATACCATCGCCGTGTGGAGCCCGCTCGACG

GGGTGGTGGCCCCGGAGACGAGCGAAGGCAGCCCCGAGCAGAGCGACGAGCGC

TTGGAGCTGGCCGTGACCCACATGGGCTTTGCGGCTAGCAAGACCGGGGCGGAG

GCAGTGGTCCGCCTGGTCGCCGCCCGCCTCTGA

SEQ ID NO: 4 (encoded by SEQ ID NO: 3):
1-letter code:
MLKPPPYGRLLRELADIPAIVTAPFRGAAKMGKLADGEPVLVLPGFLADDNATS

VLRKTFEVAGFACSGWEKGFNLGIRGDLMDYLVDRLRAVSEAAGGQKVIVVGW

SLGGLYARELGHKAPELIRMVVTLGSPFAGDLHANHAWKIYEAINSHTVDNLPIP

RDFQIKPPVHTIAVWSPLDGVVAPETSEGSPEQSDERLELAVTHMGFAASKTGAE

AVVRLVAARL-

-continued 3-letter code:
Met Leu Lys Pro Pro Pro Tyr Gly Arg Leu Leu Arg Glu Leu Ala Asp Ile Pro Ala Ile Val Thr Ala Pro Phe Arg Gly Ala Ala Lys Met Gly Lys Leu Ala Asp Gly Glu Pro Val Leu Val Leu Pro Gly Phe Leu Ala Asp Asp Asn Ala Thr Ser Val Leu Arg Lys Thr Phe Glu Val Ala Gly Phe Ala Cys Ser Gly Trp Glu Lys Gly Phe Asn Leu Gly Ile Arg Gly Asp Leu Met Asp Tyr Leu Val Asp Arg Leu Arg Ala Val Ser Glu Ala Ala Gly Gly Gln Lys Val Ile Val Val Gly Trp Ser Leu Gly Gly Leu Tyr Ala Arg Glu Leu Gly His Lys Ala Pro Glu Leu Ile Arg Met Val Val Thr Leu Gly Ser Pro Phe Ala Gly Asp Leu His Ala Asn His Ala Trp Lys Ile Tyr Glu Ala Ile Asn Ser His Thr Val Asp Asn Leu Pro Ile Pro Arg Asp Phe Gln Ile Lys Pro Pro Val His Thr Ile Ala Val Trp Ser Pro Leu Asp Gly Val Val Ala Pro Glu Thr Ser Glu Gly Ser Pro Glu Gln Ser Asp Glu Arg Leu Glu Leu Ala Val Thr His Met Gly Phe Ala Ala Ser Lys Thr Gly Ala Glu Ala Val Val Arg Leu Val Ala Ala Arg Leu In one embodiment, the palmitase enzyme used in the processes provided herein comprises an amino acid sequence of SEQ ID NO:2 and further comprises the following amino acid residue modifications D61E; R72K; V83M, R85Y, V163R and R172H.

In one embodiment, the palmitase enzyme used in the processes provided herein is encoded by a nucleic acid comprising a nucleic acid sequence of SEQ ID NO:3.

In one embodiment, the palmitase enzyme used in the processes provided herein comprises an amino acid sequence of SEQ ID NO:4.

In one embodiment, the palmitase enzyme used in the processes provided herein has an amino acid sequence of SEQ ID NO:2 and further has the following amino acid residue modifications D61E; R72K; V83M, R85Y, V163R and R172H.

In one embodiment, the palmitase enzyme used in the processes provided herein is encoded by a nucleic acid sequence of SEQ ID NO:3.

In one embodiment, the palmitase enzyme used in the processes provided herein has an amino acid sequence of SEQ ID NO:4.

Various embodiments of the process are set forth in the examples below. In each of the examples below, the shear mixer used is Ultra Turrax® T-50. The PLA1 enzyme was Lecitase® Ultra, and the PLC enzyme was Purifine®.

EXAMPLE 1

Enzymatic Process

In this example, crude soybean oil having following composition was used:
Palmitic Acid Content—10.8%
Phosphorus—567.7 ppm
Calcium—48.53 ppm
Magnesium—45.14 ppm
Free Fatty Acid 0.43%.

About 165.3 kg of crude filtered soybean oil was added to a stainless steel tank. The tank was agitated at 70 rpm at 22.8° C. Approximately 6 kg of formulated palmitase (Lot number LIP 29241-PK005, 2 kg water were added to 3 bottles containing 80 grams of powdered enzyme). The oil was shear mixed for 15 minutes with an Ultra Turrax® T-50. The tank was mixed at 70 rpm for 24 hours. About 9 kg of potassium oleate (obtained from Viva Corporation (India)) was added to the tank and shear mixed 10 min with an Ultra Turrax® T-50. Another 8 kg of formulated palmitase (Lot 29241-PK005 obtained from Verenium Corporation) as prepared above was added to the tank and shear mixed 15 minutes with an Ultra Turrax® T-50. Tank was mixed for 48 hours.

About 165.3 grams of 50% citric acid (w/w) was added and mixed for 1 hour, followed by addition of 264 grams of 10% sodium hydroxide (w/w). The contents were mixed properly. About 8.25 grams of Lecitase® Ulta PLA1 from Novozyme was added and mixed for about 2 hours. The reaction mixture was heated to 80° C., and centrifuged. The mechanical emulsion was separated in oil and aqueous layers. No separation problems were observed at this stage (approximately 14 kg of water present in system >10%). Analysis of a sample from the oil fraction showed following composition:
Palmitic Acid content 2.9%
Phosphorus—59.43 ppm
Calcium—29.09 ppm
Magnesium—16.49 ppm
Iron-below detection

EXAMPLE 2

Caustic Refining

An attempt was made to caustic refine the oil layer obtained above. The oil layer had free fatty acid (FFA) content of 12.4%. In this study, only 2 percent of the FFA was neutralized. The oil layer was heated to about 80° C.

while mixing. About 7.52 kg of 10 percent (w/w) sodium hydroxide was added and mixed slowly for 10 minutes, it unexpectedly formed an emulsion. The oil was centrifuged. However, the oil out of centrifuge was an emulsion having mayonnaise like consistency, and could not be separated into oil and aqueous layers. It was not possible to caustic refine the palmitase treated oil.

Approximately 20 liters of water was added to the emulsion and allowed to stand overnight in an attempt to separate the emulsion. It was believed that allowing the water molecules in the emulsion to have time to coalesce would separate the oil and aqueous layers. No separation was observed.

Without being bound to any particular theory, it was believed that the addition of sodium hydroxide to reduce the Free Fatty Acids (FFAs) formed a very strong emulsion with the water and the oil.

EXAMPLE 3

Physical Refining

The palmitase treated oil of Example 1 was subjected to physical refining after treatment with an acid. About 120 kg of palmitase treated oil was used in this step. About 10 kg of 50% aqueous citric acid (w/w) was added to the oil. The reaction mixture was mixed for about 30 minutes. The aqueous and oil phases were separated by centrifuging the material at 80° C. At this stage, the amount of Free Fatty Acid was about 19%, and soaps were about 304 ppm.

EXAMPLE 4

Bleaching and Deoderization

The oil phase was subjected to a bleaching step as follows: 298 grams of TrySil® S615, 995 grams of BASF FF 105, and 500 grams filter aid were added. The mixture was heated to 105° C. under 60 mbar vacuum and mixed for 30 minutes (bleacher). The oil was filtered through a plate and frame filter.

The bleached oil had FFA of about 21.15%, soap=0 ppm, phosphorus=0 ppm, peroxide value (PV)=0.0 and palmitic acid=3.7%.

The bleached oil was deodorized by heating under vacuum to 260° C. with 3% sparge steam per hour for 5 hours. The oil was cooled to 100° C. and vacuum was broken with nitrogen. Analysis of the deodorized oil showed following:
 FFA—0.45%
 PV—0.00
 Phosphorus—0 ppm
 Palmitic Acid—4.2%.

EXAMPLE 5

Enzyme Process

In this example, crude soybean oil having the following composition was used:
 Palmitic Acid Content—10.2%
 Phosphorus—681.4 ppm
 Calcium—61.2 ppm
 Magnesium—64.2 ppm
 Iron—0.59 ppm
About 127 kg of crude filtered soybean oil was added to a stainless steel tank. The tank was agitated at 70 rpm at 31° C. Approximately 8 kg of formulated palmitase (Lot number 060512, 2 kg of water were added to 4 bottles containing 80 grams of lyophilized powdered enzyme). The oil was shear mixed for 15 minutes with an Ultra Turrax® T-50. The tank was agitated at 70 rpm and covered. The oil was sampled after 45 hours reaction.

Reagent grade potassium oleate was unavailable for the testing, so a quick batch of potassium soaps were produced by adding 1.62 kg of potassium hydroxide dissolved in 1.47 kg of water. The potassium hydroxide solution was added very slowly to 8.26 kg of Refined and Bleached soybean oil. Once all of the caustic solution had been added to the oil, the caustic:oil mixture was shear mixed with Ultra Turrax® T-50 mixer for 30 minutes. The temperature increased from room temperature to about 71° C. Once the mixture had been cooled to room temperature, the potassium soaps were added to oil, approximately 6 hours after the 45 hour sample had been pulled. The oil was sampled prior to the addition of the potassium soaps.

Approximately 10 kg of formulated palmitase (Lot number 060512, 2 kg of water were added to 4 bottles containing 80 grams of lyophilized powdered enzyme). The oil was shear mixed for 15 minutes with an Ultra Turrax® T-50. The tank was agitated at 70 rpm and covered. Additional samples were pulled at 70 hours and 95 hours after the initial palmitase enzyme charge.

About 9 grams of Lecitase® Ultra (Lot number LYN05035) and about 26 grams of Purifine® PLC (Lot number 190AU008A1) were added and shear mixed for 15 minutes. About 3.81 kg of water was added and shear mixed for 15 minutes. The oil was agitated at 45-47° C. for two hours.

Approximately 4 kg of 50% (w/w) citric acid was added to the oil and shear mixed for 5 minutes. The acid was added to convert the soybean potassium soaps into fatty acids. The oil was then heated to 85° C. and centrifuged. The oil contained 304 ppm soap, so the oil was washed with 5% (w/w) hot water to remove the remaining soap.

The hot oil (approximately 85° C.) was then slowly cooled with 70 rpm agitation in a stainless steel jacketed tank with water at 4.5° C. The tank was allowed to continue cooling overnight under agitation. Approximately 14 hours later, the oil in the tank reached 8° C.

About 1.8 kg of filter aid was added to the agitated tank and allowed to become uniform, approximately 30 minutes. The cooled oil was then filtered using a plate and frame filter in order to remove the solid palmitic acid. Approximately 72 kg of palmitase treated oil was collected after filtration.

TABLE 1

| Reaction Time (hours) | Palmitic Acid (%) |
| --- | --- |
| 0 | 10.2 |
| 45 | 3.7 |
| 51 | 2.6 |
| 70 | 2.8 |
| 95 | 4.0 |

It is clear from the data in Table 1 that the quickly generated potassium soaps were not neutral and the excess potassium hydroxide deactivated the palmitase after their addition.

EXAMPLE 6

Enzyme Process

The 72 kg of palmitase treated soybean oil from Example 4 was heated to 70-72° C. in a tank. 6 kg of potassium oleate (obtained from Viva Corporation (India) Lot number POT/115) was added to the oil. 1.0 kg of soya lecithin (3FUB Lot number T180007025 from Bunge) was added and the mixture was cooled under 70 rpm agitation to 23° C.

Approximately 6.6 kg of formulated palmitase (Lot number LIP 29241PK05, 2.2 kg of water were added to 3 bottles containing 100 grams of lyophilized powdered enzyme) was added to the oil. The oil was shear mixed for 15 minutes with an Ultra Turrax® T-50. The tank was agitated at 70 rpm and covered.

Samples were pulled at 24, 48, and 72 hours reaction time and analyzed for palmitic acid. The results are in Table 2.

TABLE 2

| Reaction Time (hours) | Palmitic Acid (%) |
|---|---|
| 0 | 4.0 |
| 24 | 1.6 |
| 48 | 1.6 |
| 72 | 1.1 |

The oil was heated to 40 to 45° C. under agitation. About 36 grams of 50% (w/w) citric acid was added to the oil and shear mixed for 10 minutes. 50.1 ml of 4 normal sodium hydroxide was added to the oil and the mixture was shear mixed for 10 minutes. 3 grams of Lecitase® Ultra (Lot number LYN05035), 12 grams of Purifine® PLC (Lot number 190AU015A1), and 1 kg of water were added and shear mixed for 10 minute. The tank was covered and agitated for 4 hours to allow the phospholipases to destroy the phospholipids. 1.2 kg of 50% (w/w) citric acid was added to convert the potassium oleate to fatty acids. The oil was heated to 85° C. and centrifuged. The mechanical emulsion was separated in oil and aqueous layers.

EXAMPLE 7

Enzyme Process

In this example, crude soybean oil having the following composition was used:
Palmitic Acid Content—10.8%
Phosphorus—767.8 ppm
Calcium—71.2 ppm
Magnesium—74.9 ppm
Iron—0.7 ppm
Free Fatty Acid—0.89%

About 120 kg of crude filtered soybean oil was added to a stainless steel tank. The oil was heated to 76° C. with 70 rpm agitation, and then cooled to 23° C. Approximately 6 kg of formulated palmitase (Lot number LIP29241-PK05, 2 kg of water were added to 3 bottles containing 100 grams of lyophilized powdered enzyme) was added to the tank. The oil was shear mixed for 15 minutes with an Ultra Turrax® T-50. The tank was agitated at 70 rpm and covered. The oil was sampled after 24, 48, and 72 hours after the initial palmitase charge, and analyzed for palmitic acid content.

1.0 kg of soya lecithin (3FUB Lot number T180007025 from Bunge) and 6 kg of potassium oleate (obtained from Viva Corporation (India) Lot number POT/115) were added to the oil. The mixture was shear mixed for 15 minutes with Ultra Turrax®. Approximately 6 kg of formulated palmitase (Lot number LIP 29241PK05, 2 kg of water were added to 3 bottles containing 100 grams of lyophilized powdered enzyme). The oil was shear mixed for 15 minutes with an Ultra Turrax® T-50. The tank was agitated at 70 rpm and covered. The oil was sampled after 96 and 144 hours after the initial palmitase charge.

The oil was heated to about 45° C. About 60 grams of 50% (w/w) citric acid was added to the oil and shear mixed for 10 minutes. 100.2 ml of 4 normal sodium hydroxide was added to the oil and the mixture was shear mixed for 10 minutes. 6 grams of Lecitase® Ultra (Lot number LYN05035), 24 grams of Purifine® PLC (Lot number 190AU015A1), and 2 kg of water were added, and shear mixed for 10 minute. The tank was covered and agitated tank for 4 hours to allow the phospholipases to destroy the phospholipids. 2.4 kg of 50% (w/w) citric acid was added to convert the potassium oleate to fatty acids. The oil was heated to 85° C. and centrifuged. The mechanical emulsion was separated in oil and aqueous layers. The oil layer was analyzed for palmitic acid content.

TABLE 3

| Reaction Time (hours) | Palmitic Acid (%) |
|---|---|
| 0 | 10.8 |
| 24 | 5.7 |
| 48 | 5.1 |
| 72 | 5.1 |
| 96 | 2.5 |
| 144 | 1.9 |

EXPERIMENT 8

Palmitic Fatty Acid Removal

The palmitase treated oils from Experiments 5 and 6 were combined for removal of the palmitic acid utilizing dry fractionation. The oil:fatty acid mixture contained a total of 9.1 percent palmitic acid. The oil was heated to 80° C. under agitation to ensure the oil was completely liquid. The oil was placed in a MoBulizer™. The oil was isothermally cooled to about 10° C. with about 10° C. chilled water and held for 8 hours to allow the crystals to form (total crystallization time of 20.3 hours). The oil was then filtered using a L-Frac™ lab filter. The pressure obtained during filtration was 6 bar. The olein fraction or liquid oil obtained had a residual palmitic acid content in the mixture of 3.9% (approximately 1.5% was attached to the glycerol backbone and 2.4% were as free palmitic acid). The stearin fraction or solids obtained had a palmitic acid content of approximately 33%. The oil could then be bleached and physically refined to remove the remaining fatty acids.

While exemplary embodiments of the process have been set forth herein, other embodiments encompassing the method will be readily apparent to those skilled in the art, and all such embodiments and their equivalents are intended to be covered by this application and encompassed by the claims hereof.

What is claimed is:

1. A process for production of a low palmitic oil composition comprising
    a) mixing a triacylglycerol source at 15° C. to 50° C. with an aqueous solution of a palmitase enzyme in the presence of an emulsifier for 24 to 72 hours to obtain an emulsion, wherein the triacylglycerol comprises at least one paimitic acid residue and at least one unsaturated fatty acid residue, the emulsifier has a hydrophile-lipophile balance greater than 12 and the emulsifier comprises an alkaline salt of an unsaturated fatty acid, and the palmitase enzyme i) is encoded by the nucleic acid sequence of SEQ ID NO: 3 or ii) comprises the amino acid sequence of SEQ ID NO :4;
    b) mixing a phospholipase enzyme selected from Phospholipase A1 (PLA1), Phospholipase A2 (PLA2), Phospholipase C (PLC) and a combination thereof with the mixture of step a) to obtain a mixture comprising a degummed oil and an aqueous phase;
    c) separating the degummed oil and the aqueous phase to obtain a separated degummed oil;
    d) fractionating the degummed oil to separate free palmitic acid and a low palmitic oil by cooling the degummed oil to a temperature between −10° C. to 10° C., wherein the low palmitic oil comprises the alkaline salt of an unsaturated fatty acid;
    e) mixing a 50% aqueous citric acid with the low palmitic oil of step d) to obtain a mixture of low palmitic oil and an unsaturated fatty acid;
    f) heating the mixture of low palmitic oil and the unsaturated fatty acid from step e) to about 60° C.;
    g) mixing an acid activated bleaching earth with the mixture from step f) to form a slurry;
    h) mixing the slurry of step g) by applying a vacuum of about 100 mbar;
    i) heating the slurry of step h) to a temperature of about 90° C. to 120° C. for about 30 minutes;
    j) filtering the slurry of step i) to obtain a mixture of bleached low palmitic oil and unsaturated fatty acid;
    k) heating the mixture of step j) to up to 250° C. under a vacuum of about 0.5 to 3 mBar with about 1 to 3 percent steam based on the total weight of the mixture of step j) for about 30 to 180 minutes to obtain a deodorized low palmitic oil;
    l) cooling the deodorized low palmitic oil of step k) to about 100° C.;
    m) mixing an aqueous solution of 50 percent citric acid with the deodorized low palmitic oil of step l) to obtain a mixture of a deodorized oil and chelated metal ions; and
    n) filtering the mixture of step m) to separate the deodorized oil and chelated metal ions.

2. The process of claim 1, wherein the triacylglycerol source comprises an algal oil, vegetable oil, or an animal oil.

3. The process of claim 1, wherein the triacylglycerol source comprises soybean oil.

4. The process of claim 1, wherein the emulsifier comprises potassium oleate, sodium oleate or a combination thereof.

5. The process of claim 1, wherein the emulsifier is potassium oleate.

6. The process of claim 1, wherein the emulsifier is sodium oleate.

7. The process of claim 1, wherein the mixing of the palmitase enzyme with the triacylglycerol source is conducted at a temperature from about 20 to 50° C.

8. A process for production of a low palmitic oil composition comprising
    a) mixing a triacylglycerol source at 15° C. to 50° C. with an aqueous solution of a palmitase enzyme in the presence of an emulsifier to obtain an emulsion, wherein the triacylglycerol comprises at least one palmitic acid residue and at least one unsaturated fatty acid residue, the emulsifier has a hydrophile-lipophile balance greater than 12 and the emulsifier comprises an alkaline salt of an unsaturated fatty acid, and the palmitase enzyme i) is encoded by the nucleic acid sequence of SEQ ID NO: 3 or ii) comprises the amino acid sequence of SEQ) ID NO:4:
    b) mixing a phospholipase enzyme selected from Phospholipase A1 (PLA1), Phospholipase A2 (PLA2), Phospholipase C (PLC) and a combination thereof with the mixture of step a) to obtain a mixture comprising a degummed oil and an aqueous phase:
    c) separating the degummed oil and the aqueous phase to obtain a separated degummed oil;
    d) fractionating the degummed oil to separate free palmitic acid and a low palmitic oil by cooling the degummed oil to a temperature between −10° C. to 10°

C., wherein the low palmitic oil comprises the alkaline salt of an unsaturated fatty acid;
e) mixing a 50% aqueous citric acid with the low palmitic oil of step d) to obtain a mixture of low palmitic oil and an unsaturated fatty acid;
f) heating the mixture of low palmitic oil and the unsaturated fatty acid from step e) to about 60° C.;
g) mixing an acid activated bleaching earth with the mixture from step f) to form a slurry;
h) mixing the slurry of step g) by applying a vacuum of about 100 mbar;
i) heating the slurry of step h) to a temperature of about 90° C. to 120° C. for about 30 minutes;
j) filtering the slurry of step i) to obtain a mixture of bleached low palmitic oil and unsaturated fatty acid;
k) heating the mixture of step j) to up to 250° C. under a vacuum of about 0.5 to 3 mBar with about 1 to 3 percent steam based on the total weight of the mixture of step j) for about 30 to 180 minutes to obtain a deodorized low palmitic oil;
l) cooling the deodorized low palmitic oil of step k) to about 100° C.;
m) mixing an aqueous solution of 50 percent citric acid with the deodorized low palmitic oil of step l) to obtain a mixture of a deodorized oil and chelated metal ions; and
n) filtering the mixture of step m) to separate the deodorized oil and chelated metal ions.

9. A process for production of a low palmitic oil composition comprising
a) mixing a triacylglycerol source at 15° C. to 50° C. with an aqueous solution of a palmitase enzyme in the presence of an emulsifier to obtain an emulsion, wherein the triacylglycerol comprises at least one palmitic acid residue and at least one unsaturated fatty acid residue, the emulsifier has a hydrophile-lipophile balance greater than 12 and the emulsifier comprises an alkaline salt of an unsaturated fatty acid, and the palmitase enzyme i) is encoded by the nucleic acid sequence of SEQ ID NO: 3 or ii) comprises the amino acid sequence of SEQ ID NO:4;
b) mixing an aqueous solution of an organic acid with the emulsion of step a) to obtain a mixture having a pH of less than 4;
c) mixing an aqueous solution of a base with the mixture of step b) to obtain a mixture having a pH of about 4.5-7;
d) mixing a phospholipase enzyme selected from Phospholipase A1 (PLA1), Phospholipase A2 (PLA2), Phospholipase C (PLC) and a combination thereof with the mixture of step c) to obtain a mixture comprising a degummed oil and an aqueous phase;
e) separating the degummed oil and the aqueous phase to obtain a separated degummed oil:
f) fractionating the degummed oil to separate free palmitic acid and a low palmitic oil by cooling the degummed oil to a temperature between −10° C. to 10° C., wherein the low palmitic oil comprises the alkaline salt of an unsaturated fatty acid;
g) mixing a 50% aqueous citric acid with the low palmitic oil of step f) to obtain a mixture of low palmitic oil and an unsaturated fatty acid;
h) heating the mixture of low palmitic oil and the unsaturated fatty acid from step g) to about 60° C.;
i) mixing an acid activated bleaching earth with the mixture from step h) to form a slurry;
j) mixing the slurry of step i) by applying a vacuum of about 100 mbar;
k) heating the slurry of step j) to a temperature of about 90° C. to 120° C. for about 30 minutes;
l) filtering the slurry of step k) to obtain a mixture of bleached low palmitic oil and unsaturated fatty acid;
m) heating the mixture of step l) to up to 250° C. under a vacuum of about 0.5 to 3 mBar with about 1 to 3 percent steam based on the total weight of the mixture of step l) for about 30 to 180 minutes to obtain a deodorized low palmitic oil;
n) cooling the deodorized low palmitic oil of step m) to about 100° C.;
o) mixing an aqueous solution of 50 percent citric acid with the deodorized low palmitic oil of step n) to obtain a mixture of a deodorized oil and chelated metal ions; and
p) filtering the mixture of step o) to separate the deodorized oil and chelated metal ions.

\* \* \* \* \*

SEQUENCE LISTING

<160> NUMBER OF SEQ ID NOS: 4

<210> SEQ ID NO 1
<211> LENGTH: 684
<212> TYPE: DNA
<213> ORGANISM: Artificial Sequence
<220> FEATURE:
<223> OTHER INFORMATION: Synthetically generated

<400> SEQUENCE: 1

```
atgctgaaac cgcctcccta cggacgcctg ctgcgcgaac tggccgatat cccggccatc    60
gtgacggcac cgttccgggg cgctgcgaaa atgggcaaac tggcggatgg cgagccggta   120
ctggtgctgc ccggcttcct ggccgacgac aacgccacct cggtgctgcg caagaccttc   180
gatgtcgcgg gctttgcctg ttcgggctgg gaacgcggct tcaacctcgg cattcgtggc   240
gacctcgtgg accggctggt cgaccggctg cgggcggtgt cggaggcggc cggtggtcag   300
aaggtgatcg tggtcggctg gagcctcggc ggcctctatg cgcgcgagct gggccacaag   360
gcgcccgaac tgatccggat ggtcgtcacg ctcggcagtc cgttcgcggg cgacctccac   420
gccaaccatg cgtggaagat ctacgaggcg atcaacagcc acacggtcga caacctgccg   480
atcccggtcg atttccagat taagccgccg gtgcgcacca tcgcggtgtg gtcgccgctc   540
gacggggtgg tggcgccgga gacctcggaa ggctcgcccg agcagtcgga cgagcggcta   600
gagctggcgg tgacccacat gggctttgcc gcatcgaaga ccggggccga ggctgtggtc   660
cggctggtcg cggcgcggct ctag                                          684
```

<210> SEQ ID NO 2
<211> LENGTH: 227
<212> TYPE: PRT
<213> ORGANISM: Artificial Sequence
<220> FEATURE:
<223> OTHER INFORMATION: Synthetically generated

<400> SEQUENCE: 2

```
Met Leu Lys Pro Pro Tyr Gly Arg Leu Leu Arg Glu Leu Ala Asp
  1               5                  10                  15

Ile Pro Ala Ile Val Thr Ala Pro Phe Arg Gly Ala Ala Lys Met Gly
                 20                  25                  30

Lys Leu Ala Asp Gly Glu Pro Val Leu Val Leu Pro Gly Phe Leu Ala
             35                  40                  45

Asp Asp Asn Ala Thr Ser Val Leu Arg Lys Thr Phe Asp Val Ala Gly
         50                  55                  60

Phe Ala Cys Ser Gly Trp Glu Arg Gly Phe Asn Leu Gly Ile Arg Gly
 65                  70                  75                  80

Asp Leu Val Asp Arg Leu Val Asp Arg Leu Arg Ala Val Ser Glu Ala
                 85                  90                  95

Ala Gly Gly Gln Lys Val Ile Val Val Gly Trp Ser Leu Gly Gly Leu
            100                 105                 110

Tyr Ala Arg Glu Leu Gly His Lys Ala Pro Glu Leu Ile Arg Met Val
            115                 120                 125

Val Thr Leu Gly Ser Pro Phe Ala Gly Asp Leu His Ala Asn His Ala
        130                 135                 140

Trp Lys Ile Tyr Glu Ala Ile Asn Ser His Thr Val Asp Asn Leu Pro
145                 150                 155                 160

Ile Pro Val Asp Phe Gln Ile Lys Pro Pro Val Arg Thr Ile Ala Val
                165                 170                 175
```

Trp Ser Pro Leu Asp Gly Val Val Ala Pro Glu Thr Ser Glu Gly Ser
            180                 185                 190

Pro Glu Gln Ser Asp Glu Arg Leu Glu Leu Ala Val Thr His Met Gly
        195                 200                 205

Phe Ala Ala Ser Lys Thr Gly Ala Glu Ala Val Val Arg Leu Val Ala
    210                 215                 220

Ala Arg Leu
225

<210> SEQ ID NO 3
<211> LENGTH: 684
<212> TYPE: DNA
<213> ORGANISM: Artificial Sequence
<220> FEATURE:
<223> OTHER INFORMATION: Synthetically generated

<400> SEQUENCE: 3
atgctcaagc cccaccttta cggccgtctg ctccgcgaac tggctgatat cccggcgatc      60
gtgactgctc cgttccgcgg cgcagccaaa atgggcaaac tggctgatgg cgagccggta     120
ctggtgctgc cggcttcct ggcggacgac aacgcgacca gcgtgctgcg aagaccttc       180 gaggtcgccg gctttgcgtg cagcggctgg gaaaagggct tcaacctcgg cattcgtggc     240
gacctcatgg actacctggt cgaccgcctg cgcgccgtga gcgaggccgc ggggggggcag    300 aaggttatcg tggtcggctg gagtctcggc ggcctctacg cccgggagct tggccacaag    360
gcccccgaac tgatcaggat ggtcgtcacg ctcggctctc cgttcgccgg cgacctccac    420
gcgaaccatg cctggaagat ctacgaggcc atcaactccc acacggtcga caacctgccg    480
atcccgcgcg atttccagat taagccgccg gtgcatacca tcgccgtgtg gagcccgctc    540
gacggggtgg tggcccccgga acgagcgaa ggcagccccg agcagagcga cgagcgcttg    600
gagctggccg tgacccacat gggctttgcg gctagcaaga ccggggcgga ggcagtggtc    660
cgcctggtcg ccgcccgcct ctga                                           684

<210> SEQ ID NO 4
<211> LENGTH: 227
<212> TYPE: PRT
<213> ORGANISM: Artificial Sequence
<220> FEATURE:
<223> OTHER INFORMATION: Synthetically generated

<400> SEQUENCE: 4

Met Leu Lys Pro Pro Tyr Gly Arg Leu Leu Arg Glu Leu Ala Asp
  1               5                  10                  15

Ile Pro Ala Ile Val Thr Ala Pro Phe Arg Gly Ala Ala Lys Met Gly
            20                  25                  30

Lys Leu Ala Asp Gly Glu Pro Val Leu Val Leu Pro Gly Phe Leu Ala
        35                  40                  45

Asp Asp Asn Ala Thr Ser Val Leu Arg Lys Thr Phe Glu Val Ala Gly
    50                  55                  60

Phe Ala Cys Ser Gly Trp Glu Lys Gly Phe Asn Leu Gly Ile Arg Gly
 65                  70                  75                  80

Asp Leu Met Asp Tyr Leu Val Asp Arg Leu Arg Ala Val Ser Glu Ala
                85                  90                  95

Ala Gly Gly Gln Lys Val Ile Val Val Gly Trp Ser Leu Gly Gly Leu
            100                 105                 110

Tyr Ala Arg Glu Leu Gly His Lys Ala Pro Glu Leu Ile Arg Met Val
        115                 120                 125

```
Val Thr Leu Gly Ser Pro Phe Ala Gly Asp Leu His Ala Asn His Ala
    130             135             140

Trp Lys Ile Tyr Glu Ala Ile Asn Ser His Thr Val Asp Asn Leu Pro
145             150             155             160

Ile Pro Arg Asp Phe Gln Ile Lys Pro Pro Val His Thr Ile Ala Val
            165             170             175

Trp Ser Pro Leu Asp Gly Val Val Ala Pro Glu Thr Ser Glu Gly Ser
        180             185             190

Pro Glu Gln Ser Asp Glu Arg Leu Glu Leu Ala Val Thr His Met Gly
            195             200             205

Phe Ala Ala Ser Lys Thr Gly Ala Glu Ala Val Val Arg Leu Val Ala
    210             215             220

Ala Arg Leu
225
```